United States Patent [19]
Graham

[11] Patent Number: 5,585,635
[45] Date of Patent: Dec. 17, 1996

[54] INFRARED GAS ANALYZER AND METHOD

[75] Inventor: James E. Graham, Brookfield, Wis.

[73] Assignee: Marquette Electronics, Inc., Milwaukee, Wis.

[21] Appl. No.: 312,114

[22] Filed: Sep. 26, 1994

[51] Int. Cl.⁶ .................................................. G01N 21/61
[52] U.S. Cl. ........................................................ 250/343
[58] Field of Search .............................. 250/343, 338.5

[56] References Cited

U.S. PATENT DOCUMENTS

| | | | |
|---|---|---|---|
| 3,725,701 | 4/1973 | Link | 250/43.5 |
| 3,793,525 | 2/1974 | Burch et al. | 250/343 |
| 4,013,260 | 3/1977 | McClatchie et al. | 250/343 |
| 4,027,972 | 6/1977 | Davies | 356/51 |
| 4,103,174 | 7/1978 | McClatchie et al. | 250/493 |
| 4,163,899 | 8/1979 | Burough | 250/343 |
| 4,177,381 | 12/1979 | McClatchie et al. | 250/343 |
| 4,200,791 | 4/1980 | Burough | 250/343 |
| 4,205,913 | 6/1980 | Ehrfeld et al. | 250/343 |
| 4,233,513 | 11/1980 | Elder et al. | 250/343 |
| 4,346,296 | 8/1982 | Passaro et al. | 250/343 |
| 4,398,091 | 8/1983 | Passaro | 250/343 |
| 4,437,004 | 3/1984 | Passaro et al. | 250/343 |
| 4,480,190 | 10/1984 | Burough et al. | 250/343 |
| 4,577,105 | 3/1986 | Krempl et al. | 250/343 |
| 4,578,762 | 3/1986 | Wong | 364/497 |
| 4,579,568 | 4/1986 | Ricciardelli et al. | 155/189 |
| 4,592,368 | 6/1986 | Ricciardelli et al. | 128/719 |
| 4,598,201 | 7/1986 | Fertig et al. | 250/343 |
| 4,687,934 | 8/1987 | Passaro et al. | 250/343 |
| 4,692,621 | 9/1987 | Passaro et al. | 250/343 |
| 4,713,095 | 12/1987 | Ricciardelli | 55/189 |
| 4,742,229 | 5/1988 | Weinel | 250/343 |
| 4,817,013 | 3/1989 | Corenman et al. | 364/497 |
| 4,829,183 | 5/1989 | McClatchie et al. | 250/346 |
| 4,885,469 | 12/1989 | Yamagishi et al. | 250/345 |
| 4,899,053 | 2/1990 | Lai et al. | 250/343 |
| 4,907,166 | 3/1990 | Corenman et al. | 364/497 |
| 4,914,719 | 4/1990 | Conlon et al. | 250/339 |
| 4,981,362 | 1/1991 | deJong et al. | 356/436 |
| 5,036,198 | 7/1991 | Spaeth | 250/343 |
| 5,046,018 | 9/1991 | Flewelling et al. | 364/497 |
| 5,049,170 | 9/1991 | Parnoff | 55/323 |
| 5,129,401 | 7/1992 | Corenman et al. | 128/716 |
| 5,146,283 | 9/1992 | Parnoff et al. | 356/246 |
| 5,231,591 | 7/1993 | Flewelling et al. | 364/497 |

FOREIGN PATENT DOCUMENTS

| | | |
|---|---|---|
| 2618554A1 | 7/1987 | France . |
| 149949 | 8/1985 | Japan .................. 250/343 |
| 2165941 | 4/1986 | United Kingdom .............. 250/343 |

Primary Examiner—Carolyn E. Fields
Attorney, Agent, or Firm—Michael, Best & Friedrich

[57] ABSTRACT

An infrared gas analyzer and method employing one optical path which includes one infrared source, one sample cell containing the gas(es) to be analyzed, one infrared sensor and one infrared filter no matter how many gases are to be analyzed. The one optical path with one filter is utilized for both determining infrared source output and infrared absorption by the gas(es) to be measured.

9 Claims, 2 Drawing Sheets

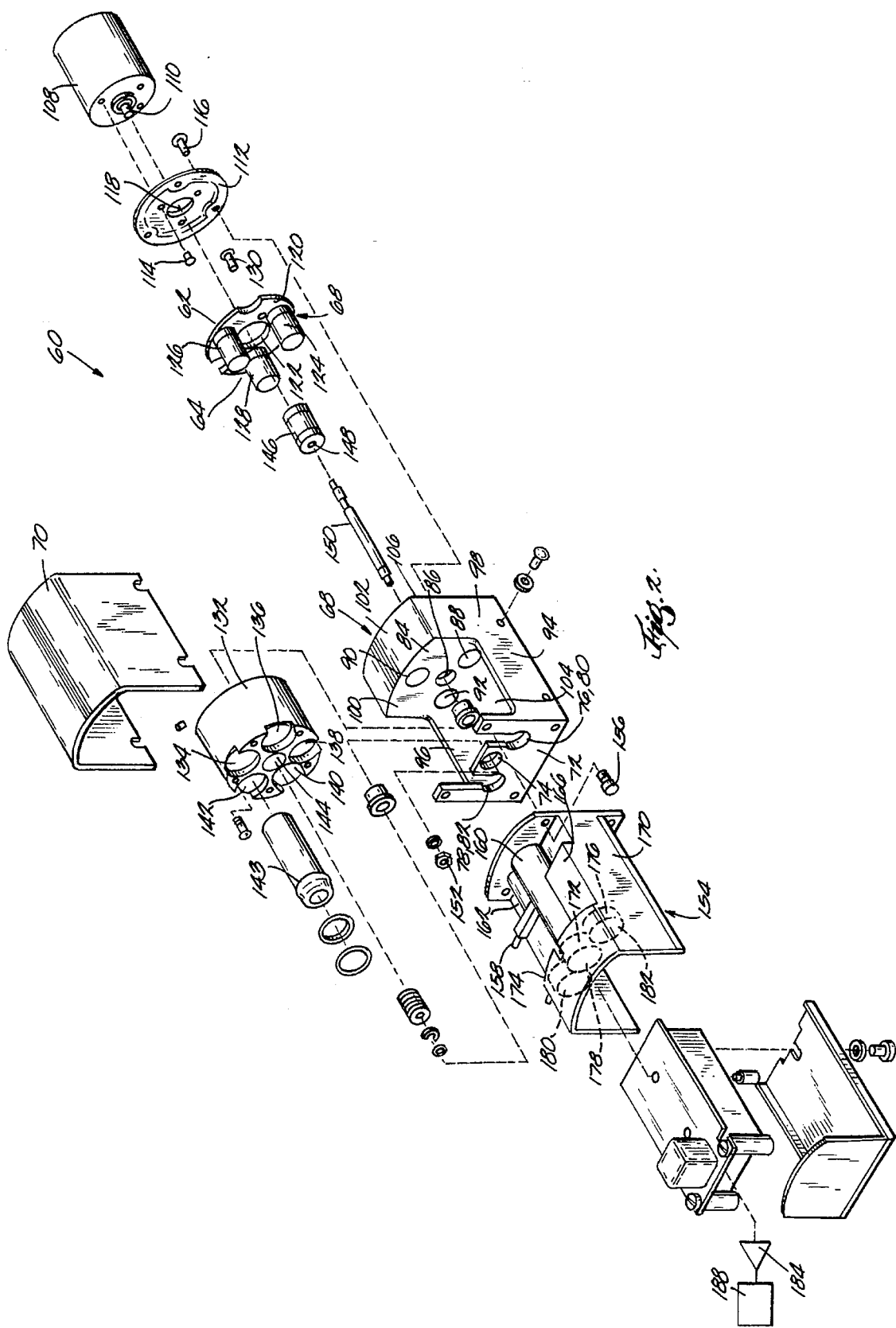

INFRARED GAS ANALYZER AND METHOD

FIELD OF THE INVENTION

The invention relates to infrared gas analyzers.

BACKGROUND OF THE INVENTION

Generally, when using infrared energy to measure gas amounts within a sample, the infrared energy passes through the sample in a sample cell and is detected by an infrared sensor. The infrared energy will be reduced by the presence of any gas that absorbs infrared energy. The wavelength band of the beam of infrared energy passing through the sample cell containing the gas sample is changed periodically by the selective interposition of one or more filters in the path of the beam. The filters are usually carried on a rotatable wheel. Typically, each filter passes only radiation at a narrow band corresponding to a characteristic absorption wavelength band of a particular gas of interest. Therefore, through use of an infrared filter that is selected for each gas to be monitored in the gas sample, only infrared energy that can be absorbed by that gas is allowed to pass through the filter and be detected by the sensor.

With this arrangement, ideally the only infrared energy changes, as compared to the infrared energy detected when the gas to be monitored is not present, would be caused by the particular gas to be monitored. However, in practice and as one example, the changes in infrared energy detected may be caused by the infrared source itself changing its power output. The power output of the infrared source can change as the gas analyzer as a whole heats up and as the power source ages. To ensure accuracy in gas analysis, these types of changes in the infrared source power output have to be handled in some particular manner.

Several methods for handling the power output changes in the infrared source are known such as served heaters, extra sensors and stopping the gas analysis frequently to recalibrate the analyzer. These methods are typically complex and costly and have one thing in common, they try to monitor the infrared power output of the infrared source by reading it with some other sensor or some other path not changed by the gases to be monitored. The problem inherent in these methods lies in the fact that a different sensor/path from that of the sensor/path analyzing the gases is used to monitor changes in the power output of the infrared source. Because a different sensor/path is utilized, these methods are not the most accurate.

For example, one particular method of determining infrared source output is to use a second or additional filter to look at a wavelength in the infrared spectrum that is not changed by the gas to be monitored or any other gas that could be in the sample cell when the gas analyzer unit is in normal use. This method however may not produce the best results for the following reasons. As the infrared source ages, the power output spectra changes. Therefore, wavelength where gas absorption is being checked may change in one direction and the wavelength where power level changes may change in the other direction.

Another problem with gas analyzers is the susceptibility of filters to heat. All infrared filters are affected by heat. With changes in temperature, these filters shift in the spectra being passed and change in transmittance so that some of the gas absorption signal they are designed to pass will be lost when the filter shifts.

The use of served heaters minimizes changes within the infrared analyzer, however, significantly increased cost, power consumption and heat buildup makes served heaters not a preferred method for minimizing changes in power output of the infrared source.

SUMMARY OF THE INVENTION

Therefore, there is a need for a better infrared gas analyzer and method that will more accurately handle changes in temperature and infrared source power output. The present invention is an analyzer and method for analyzing gases that employs one optical path which includes one infrared source, one sample cell containing the gas(es) to be analyzed, one infrared sensor and one infrared filter no matter how many gases are to be analyzed. The one optical path with one filter is utilized for both determining infrared source output and infrared absorption by the gas(es) to be measured. The filter is a wideband bandpass filter that is selected to pass the necessary gas spectra points of the gas(es) to be analyzed as well as two spectra sidebands which are the additional spectra on each side of the gas spectra points. Due to the wideband of energies passed by the filter, the gas spectra points of interest will not be lost when the filter shifts in the spectra due to changes in the environmental temperature or age. Further, the two sidebands are utilized as a non-changing infrared power level indicator.

In order to determine amounts and changes in gas concentrations with only one filter, reference cells containing known quantities of particular gases are used as negative filters. The reference cells are mounted to be selectively interposed in the optical path one reference cell at a time. With that arrangement the infrared sensor takes a number of readings of the energy reaching the sensor, i.e. a reading as each reference cell is interposed in the optical path. The information obtained from the multiple readings is analyzed to determine the presence and/or amount of gases being monitored. For example, a microprocessor analyzes the energy readings from the sensor and determines the concentration of gases that are in the sample cell.

It is one object of the invention to provide a gas analyzer and method that can more accurately handle changes in the infrared source power output and/or changes in temperature within the analyzer.

It is another object of the invention to provide a gas analyzer and method that can more accurately handle filter spectra shift.

It is another object of the invention to provide a more accurate gas analyzer and method having a simplified construction.

It is another object of the invention to provide a gas analyzer and method that utilizes the same optical path to determine both infrared source output and infrared absorption by the gas(es) to be analyzed.

It is another object of the invention to provide a gas analyzer and method that uses one filter to pass the necessary gas spectra points of the gas(es) to be analyzed as well as two spectra sidebands which provide additional spectra on each side of the gas spectra points.

It is another object of the invention to provide a gas analyzer and method that uses one filter that will not lose gas spectra points even when the filter shifts in the spectra due to changes in the environmental temperature or age of the filter.

It is another object of the invention to provide a gas analyzer and method that uses the two sidebands being passed by the one filter as a non-changing infrared power level indicator.

It is another object of the invention to provide a gas analyzer and method that uses one filter such that if the filter shifts in the spectra, the indicator of infrared power output remains the same.

Other features and advantages of the invention will become apparent to those of ordinary skill in the art upon review of the following detailed description, claims, and drawings

BRIEF DESCRIPTION OF THE DRAWINGS

FIG. 2 is an exploded schematic of a unit including three analyzers embodying the invention.

Figure 1:
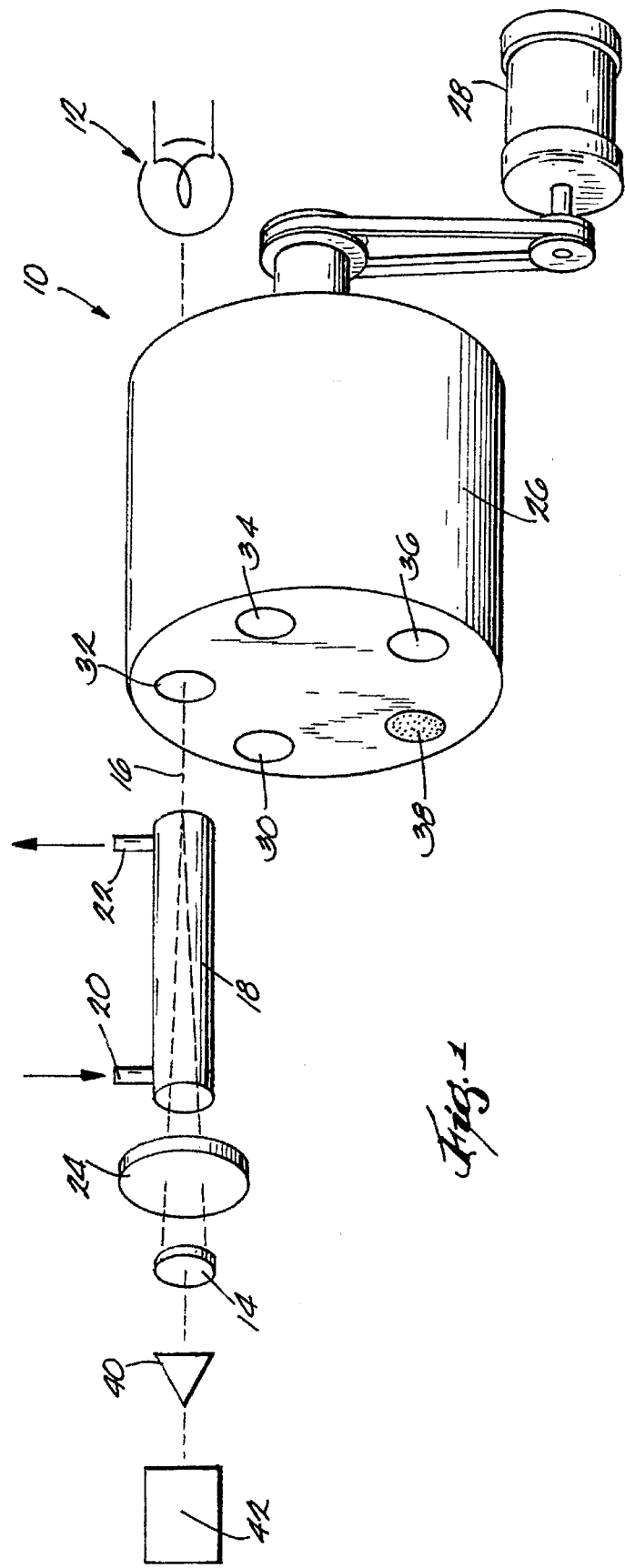
FIG. 1 is an exploded schematic of an analyzer embodying the invention.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Referring to FIG. 1, there is shown an infrared gas analyzer 10 embodying the invention. The analyzer 10 will be described in relation to the analysis of four anesthetic agents; halothane, enflurane, isoflurane and sevoflurane. However, it should be noted that the analyzer 10 of the present invention may be used to analyze other combinations of gases.

The analyzer 10 includes an infrared source 12 such as 5 v flashlight bulb. In line with the infrared source 12 is an infrared sensor 14 such as the infrared detector manufactured by Graseby of Orlando, Fla. as part number 1500115. The path of infrared light between the infrared source 12 and the infrared sensor 14 defines an optical path 16.

Disposed in the optical path 16 is a sample cell 18 that contains the gas mixture to be analyzed. Typically, the gas mixture to be analyzed is the breath of an anesthetized subject. The sample cell 18 has a gas inlet 20 which enables the gas mixture to enter the sample cell 18 and a gas outlet 22 which enables the gas mixture to exit the sample cell 18. The dimensions of the sample cell 18 are chosen so as to optimize both response time and sensitivity of analyzer 10. Sensitivity and response time are effected by the length of a sample cell. That is, a sample cell which is too long results in increased sensitivity however with decreased response time and a sample cell which is too short results in increased response time however with decreased sensitivity. The dimensions of a sample cell are thus chosen with proper consideration for response time and sensitivity and are selected between what would be the lengths that would provide either the best response time or the best sensitivity, i.e. that length which affords the best of both. For example, the four anesthetic agents halothane, enflurane, isoflurane and sevoflurane have poor absorption characteristics and thus require a longer sample cell. Assuming a flow rate of the gas mixture of about 200 ml/min, the sample cell 18 which may contain the above-identified four anesthetic agents preferably has the following dimensions: 0.249"×2.02".

Further disposed in the optical path 16 is a single infrared filter 24. To ensure accuracy in gas analysis, changes in the infrared source power output are handled by analyzer 10 through use of the filter 24. Filter 24 is thus utilized for determining both infrared source output and infrared absorption by the gases to be measured. The use of only one filter 24 leads to more accurate gas measurements because the same optical path 16 is used to determine both infrared source energy and adsorption.

Preferably, filter 24 is a bandpass filter that is selected so as to pass a wider band of energies than just the absorption spectra of the gases analyzer 10 is designed to analyze. Such a single wideband filter 24 passes the necessary gas spectra points which cannot be lost even if filter 24 shifts in the spectra due to changes in the environmental temperature or changes due to age of the power source. Further, filter 24 is selected to pass two sidebands, i.e., additional spectra on each side of the gas spectra points of interest. The two sidebands are utilized as a non-changing infrared power level indicator. If filter 24 shifts in the spectra it is designed to pass, the sideband energy remains the same.

More particularly, filter 24 is selected to pass the expected absorption spectra of the gases to be analyzed. In addition, the filter is selected to pass additional spectra on each side of the gap absorption spectra, i.e., sidebands. The width of the sidebands passed by filter 24 is determined on the basis of expected filter and/or power output variances and the magnitude thereof and the width is such as to accommodate normal, expected operational conditions. Therefore, should the analyzer temperature or power source output vary, the variances are accommodated in the sidebands and does not effect the operation and accuracy of analyzer 10. The use of a single wideband filter incorporating both the absorption spectra of the gas to be analyzed and the predetermined sidebands, affects the additional advantage that should, for example, temperature move the filter in one direction and the aging power source in an opposite direction, the sideband would still surround the absorption spectra of the gases to be analyzed.

In the example using the four anesthetic gases halothane, enflurane, isoflurane and sevoflurane, these gases absorb infrared energy in the range of 3.2–3.4 microns. The filter 24 is thus chosen to pass the energy in the range of 3.16–3.5 microns which includes the gas spectra points of interest and two sidebands.

By using one filter 24 in analyzer 10, it is possible for analyzer 10 to be constructed with one infrared source 12 and one sample cell 18 in the optical path 16. With this construction, there can be no difference in the infrared sensor 14 output for use as a gas absorption indicator that will not also affect the sensor 14 output for use as a reference of infrared source power. Accordingly, in order to determine changes in gas concentrations with one filter 24, reference cells filled with known quantities of the particular gases to be measured are used for negative filtering which will be explained in greater depth hereafter. The number of reference cells needed is dependent upon the number of gases to be analyzed by the analyzer. Preferably, there should be one reference cell filled with a zero gas such as air that does not absorb any infrared energy and one reference cell that corresponds to each of the gases to be analyzed. The reference cells that are devoted to a specific gas are filled with a known quantity of that gas. Preferably, such reference cells are mounted on a rotatable element such that only one reference cell at a time is disposed in the optical path 16.

In analyzer 10 of FIG. 1, a rotating cylinder 26 is disposed in the optical path 16. The rotatable cylinder 26 is connected to a conventional motor 28 so as to effectuate the rotation of the cylinder 26. The cylinder 26 has therein five bores 30, 32, 34, 36 and 38 that are equidistantly spaced from one another. Bores 30, 32, 34, 36, and 38 are adapted to removeably house a reference cell. As the cylinder 26 is rotated by motor 28, the housed reference cells are sequentially disposed in the optical path 16 one at a time.

In the analyzer 10 of FIG. 1, the bores 30, 32, 34, 36 and 38 contain reference cells. In order to analyze the four anesthetic agents halothane, enflurane, isoflurane and sevoflurane, in the preferred embodiment, A, H, E, F and S, reference cells A, H, E, F and S are filled as follows at a pressure of 760 mmHg:

| reference cell A = | 100.0% air | 760.0 mmHg |
|---|---|---|
| reference cell H = | 27.1% halothane | 205.9 mmHg |
| | 2.0% $N_2O$ | 15.2 mmHg |
| | 55.9% air | 424.9 mmHg |
| | 15.0% He | 114.0 mmHg |
| reference cell E = | 19.4% enflurane | 147.6 mmHg |
| | 2.0% $CO_2$ | 15.2 mmHg |
| | 2.0% $N_2O$ | 15.2 mmHg |
| | 61.6% air | 468.0 mmHg |
| | 15.0% He | 114.0 mmHg |
| reference cell F = | 26.1% isoflurane | 198.4 mmHg |
| | 2.0% $CO_2$ | 15.2 mmHg |
| | 56.9% air | 432.4 mmHg |
| | 15.0% He | 114.0 mmHg |
| reference cell S = | 17.4% sevoflurane | 132.2 mmHg |
| | 67.6% air | 513.8 mmHg |
| | 15.0% He | 114.0 mmHg |

Helium is included in reference cells H, E, F and S to provide a means to determine the leak rate of the reference cells by measurement of the helium leaking from each reference cell. Helium does not effect the operation of analyzer 10 because it does not absorb infrared energy.

The analyzer 10 of FIG. 1 operates as follows with reference to the example using the four anesthetic gases halothane, enflurane, isoflurane and sevoflurane. The reference cells A, H, E, F and S are filled with the quantities of the gases shown previously. The sample cell 18 is filled with the gas mixture to be analyzed via inlet 20. The cylinder 26 is then rotated by the motor 28 so as to sequentially dispose reference cells A, H, E, F and S in the optical path 16 one at a time. As each reference cell A, H, E, F and S is in the optical path 16, energy from the infrared source 12 passes through the reference cell A, H, E, F or S, through the sample cell 18, through the filter 24 then is detected by the infrared sensor 14. Therefore, for one rotation of the cylinder 26, five energy readings are taken by the infrared sensor 14 corresponding to each of the five reference cells A, H, E, F and S. The sensor readings are denoted as follows:

| Reference Cell | Sensor Reading Designation |
|---|---|
| A | $E_A$ |
| H | $E_H$ |
| E | $E_E$ |
| F | $E_F$ |
| S | $E_S$ |

The infrared sensor 14 is electrically connected to a pre-amplifier 40 which itself is electrically connected to a 32 bit microprocessor 42. The sensor readings are thus amplified by pre-amplifier 40 then sent to microprocessor 42 to compute the gas concentrations for the various gases.

Gas concentrations are determined through use of negative filtering. Negative filtering is where one filters out the spectra being used and keeps the part of the spectra that is not absorbed by the gas to be measured. The negative filtering reading when subtracted from the sensor reading without the negative filtering will give the total inband infrared energy after absorption. In other words, a reading is taken through the sample cell without any filtering. A second reading is taken but based on all of the gases present with the exception of that for which a quantitative reading is desired. A comparison of those two readings gives a measure of the amount of the gas for which the reading is desired. As will be evident from the discussion to follow, the gas concentration figures are determined mathematically via predetermined equations.

More specifically, to determine the concentration of for example halothane, the reading $E_A$ (which corresponds to only the gases in the sample cell absorbing energy) is used with the reading $E_H$ (which corresponds to the both the gas in reference cell H and gases in the sample cell absorbing energy). The mathematical equations used to determine the concentrations of each of the four agents in the example are as follows:

(1) Halothane $$\alpha_{HH}\eta_H + \alpha_{HE}^1\eta_E + \alpha_{HF}^1\eta_F + \alpha_{HS}^1\eta_S =$$

$$\frac{1}{L_A} \ln \frac{\left(1 - \frac{E_H}{E_A}\right)\left(1 - \left[\frac{\Delta V_a}{\Delta V_F}\right]_H\right)}{\left[\frac{\Delta V_a}{\Delta V_F}\right]_H \left(\frac{E_H}{E_A} - e^{-\alpha_{HH}L_R\eta_R}\right)}$$

(2) Enflurane $$\alpha_{EH}^1\eta_H + \alpha_{EE}\eta_E + \alpha_{EF}^1\eta_F + \alpha_{ES}^1\eta_S =$$

$$\frac{1}{L_A} \ln \frac{\left(1 - \frac{E_E}{E_A}\right)\left(1 - \left[\frac{\Delta V_a}{\Delta V_F}\right]_E\right)}{\left[\frac{\Delta V_a}{\Delta V_F}\right]_E \left(\frac{E_E}{E_A} - e^{-\alpha_{EE}L_R\eta_R}\right)}$$

(3) Isoflurane $$\alpha_{FH}^1\eta_H + \alpha_{FE}^1\eta_E + \alpha_{FF}\eta_F + \alpha_{FS}^1\eta_S =$$

$$\frac{1}{L_A} \ln \frac{\left(1 - \frac{E_F}{E_A}\right)\left(1 - \left[\frac{\Delta V_a}{\Delta V_F}\right]_F\right)}{\left[\frac{\Delta V_a}{\Delta V_F}\right]_F \left(\frac{E_A}{E_A} - e^{-\alpha_{FF}L_R\eta_R}\right)}$$

(4) Sevoflurane $$\alpha_{SH}^1\eta_H + \alpha_{SE}^1\eta_E + \alpha_{SF}^1\eta_F + \alpha_{SS}\eta_S =$$

$$\frac{1}{L_A} \ln \frac{\left(1 - \frac{E_S}{E_A}\right)\left(1 - \left[\frac{\Delta V_a}{\Delta V_F}\right]_S\right)}{\left[\frac{\Delta V_a}{\Delta V_F}\right]_S \left(\frac{E_S}{E_A} - e^{-\alpha_{SS}L_R\eta_R}\right)}$$

where $\eta_H$=concentration of halothane in sample cell $\eta_E$=concentration of enflurane in sample cell $\eta_F$=concentration of isoflurane in sample cell $\eta_S$=concentration of sevoflurane in sample cell $\eta_R$=concentration of the halothane, enflurane, isoflurane or sevoflurane in reference cell $\alpha_{HH}$=absorption coefficient of halothane averaged over the absorption band $\alpha_{EE}$=absorption coefficient of enflurane averaged over the absorption band $\alpha_{FF}$=absorption coefficient of isoflurane averaged over the absorption band $\alpha_{SS}$=absorption coefficient of sevoflurane averaged over the absorption band $\alpha_{HE}$=averaged absorption coefficient $\alpha_{HF}$=averaged absorption coefficient $\alpha_{HS}$=averaged absorption coefficient $\alpha_{EH}$=averaged absorption coefficient $\alpha_{EF}$=averaged absorption coefficient $\alpha_{ES}$=averaged absorption coefficient $\alpha_{FH}$=averaged absorption coefficient $\alpha_{FE}$=average absorption coefficient $\alpha_{FS}$=average absorption coefficient $\alpha_{SH}$=average absorption coefficient $\alpha_{SE}$=average absorption coefficient $\alpha_{SF}$=average absorption coefficient $L_A$=length of sample cell $L_R$=length of reference cell $\Delta V_a$=frequency width of absorption band $\Delta V_F$=frequency width of filter $E_A$=energy incident on detector with reference cell A in optical path $E_H$=energy incident on detector with reference cell H in optical path $E_E$=energy incident on detector with reference cell E in optical path $E_F$=energy incident on detector with reference cell F in optical path $E_S$=energy incident on detector with reference cell S in optical path $$\frac{\Delta V_a}{\Delta V_F}$$

for each of the four gases in this example must be determined in calibration experiments. The absorption by a high concentration of agent on a reference cell will change the spectral distribution of the energy incident on the sample cell thus the absorption coefficients are not constants. Therefore, the average absorption coefficients or matrix elements $\alpha_{HH}$, $\alpha_{EE}$, $\alpha_{FF}$ and $\alpha_{SS}$ are determined in experiments with only one gas present. The remainder of the average absorption coefficient must also be determined by calibration experiments. With all the calibration work done, the four equations can be solved for the unknown concentrations of the four agents in the sample cell, i.e., $\eta_H$, $\eta_E$, $\eta_F$, and $\eta_S$.

The analyzer 10 of the present invention, which employs one infrared filter 24 for sensing both infrared power output and gas absorption, is thus not sensitive to temperature and able to operate after a cold start-up without a delay for warm-up. The analyzer 10 can also operate at any infrared power level output of the infrared source 12 since it does not matter whether through aging or temperature the power output of the infrared source 12 shifts either up or down the spectra. Further, since no heating or cooling units are needed to maintain a consistent temperature, the analyzer 10 utilizes less power and can be very small in size and light weight.

Due to the ability of the present invention to be small in size, this allows other analyzers to be present in a single unit. Referring now to FIG. 2, there is shown a gas analyzer unit 60 employing the present invention which is actually three independent analyzers 62, 64 and 66 in the same unit 60. Each of the independent analyzers 62, 64 and 66 operates analogously to the analyzer 10 of FIG. 1 and each defines one optical path having a single infrared source, a single sample cell, a single filter and a single infrared detector. Yet each analyzer 62, 64 and 66 analyzes a different gas(es). The three analyzers 62, 64 and 66 share only common reference cells and data processing components. The three analyzers 62, 64 and 66 of the unit 60 can analyze any gases, however, the unit 60 depicted in FIG. 2 analyzes the following gases. The first analyzers 62 analyses carbon dioxide. The second analyzer 64 analyses nitrous oxide. The third analyzer 66 is substantially identical to the analyzer 10 of FIG. 1 in that it is designed to analyze the following four anesthetic gases; halothane, enflurane, isoflurane and sevoflurane.

The structure of the unit 60 is as follows with reference to FIG. 2. The unit 60 has a first housing 68 with a removable cover 70. The housing 68 has an end wall 72 having a central aperture 74. On each side of the aperture 74 is a slot 76 and 78 that terminates in an aperture 80 and 82 respectively. The housing 68 has another end wall 84 having a central aperture 86 that is axially aligned with the aperture 74 of the end wall 72. The end wall 84 also has therein three apertures 88, 90 and 92 surrounding the central aperture 86. Apertures 88 and 92 are coaxially aligned with apertures 80 and 82 respectively on the end wall 72. Side walls 94 and 96 connect the end walls 72 and 84 of the housing 68. A portion 98 and 100 of each side wall 94 and 96 respectively extends beyond the end wall 84 and are connected via a top wall 102. The side walls 94 and 96 and the end walls 72 and 84 define a recess 104 and the portions of the side wall 98 and 100, the end wall 84 and the top wall 102 define a recess 106.

A motor 108 is housed in the recess 106. The motor 108 has a bracket 110 on one end. A mounting plate 112 is used to secure the motor 108 to the end wall 84 in that the motor 108 is secured to the plate 112 with screws 114 and the plate 112 is secured to the end wall 84 of the housing 68 with screws 116. The mounting plate 112 has a central aperture 118 through which extends the bracket 110 of the motor 108. The aperture 118 is coaxially aligned with the aperture 86 in the end wall 84. Also attached to the end wall 84 is a second plate 120. The plate 120 has therein a central aperture 122 that is coaxially aligned with the aperture 118 in the plate 112 and the aperture 86 in the end wall 84. The plate 120 has thereon three infrared sources 124, 126 and 128 such as 5 v flashlight bulbs. The three infrared sources 124, 126 and 128 are spaced on the plate 120 such that when the plate 120 is secure to the end wall 84 with screws 130, the three infrared sources 124, 126 and 128 align with and extend through the apertures 88, 90 and 92 respectively in the end wall 84 and partially into the recess 104.

A rotatable cylinder 132 is housed in recess 104. The cylinder 132 has therein five bores 134, 136, 138, 140 and 142 equidistantly spaced. Each bore 134, 136, 138, 140 and 142 is adapted to removeably house a reference cell 143 filled with a known quantity of a certain gas. The cylinder 132 also has therein a central bore 144 which is axially aligned with the aperture 86 in the end wall 84 and the aperture 118 in the mounting plate 112. The removable cover 70 enables access to the rotating cylinder 132 and the reference cells 143.

The motor 108 is connected to the cylinder 132 to enable the cylinder 132 to rotate within the recess 104 as follows. A barrel 146 is positioned in the central bore 144 of the cylinder 132. The barrel 146 has therein a central bore 148. A rod 150 connects the motor 108 and the cylinder 132. One end of the rod 150 connects to the bracket 110 on the motor 108. The rod 150 extends through aperture 118 in plate 112, through aperture 122 in the plate 120, through aperture 86 in the end wall 84, through aperture 148 in the barrel 146, and is secured at the other end with a nut 152. The motor 108 rotates the rod 150 which in turn rotates the cylinder 132 in the recess 104.

The unit 60 also includes a second housing 154. The second housing 154 is secured to the first housing 68 via screws 156. The second housing 154 includes a gas inlet 158. In communication with the gas inlet 158 is a sample cell 160. Sample cell 162 is in communication with the sample cell 160 via a conduit (not shown). Sample cell 166 is in communication with sample cell 162 via a conduit (not shown). A gas outlet (not shown) is in communication with the sample cell 166 and enables gas to exit from the second housing 154. The gas to be monitored enters the unit 60 at the inlet 158, travels through the sample cells 160, via a conduit to sample cell 162, via a conduit to sample cell 166 then exits the unit 60 via the outlet.

At the end of the sample cells 160, 162 and 166 is a single filter 172, 174 and 176 respectively. To ensure accuracy in gas analysis, the changes in the infrared source power output are handled by each of the three analyzers 62, 64 and 66 through use of one filter per analyzer. The one filter per analyzer is utilized for the same purpose as analyzer 10 of FIG. 1 that being for determining both infrared source output and infrared absorption by the gas(es) to be measured. The use of only one filter per analyzer leads to more accurate gas measurements for each analyzer because the same optical path is used to determine both infrared source energy and energy absorption. Each filter 172, 174 and 176 is chosen to be a bandpass filter that passes a wideband of energies. Such a single wideband filter passes the necessary gas spectra points which will not be lost even when the filter shifts in the spectra due to changes in the environmental temperature or changes due to age of the power source. Further, such a wideband filter is selected to pass two sidebands which are additional spectra on each side of the gas spectra points of interest. The two sidebands are utilized as a non-changing infrared power level indicator.

The unit 60 further includes an infrared sensor 178, 180 and 182 per analyzer 62, 64 and 66 respectively. The filters 172, 174 and 176 are cap-type filters which are attached to the sensor 178, 180 and 182 respectively and can be of the type manufactured by OCLI. The infrared sensors 178, 180 and 182 can be of the type manufactured by Graseby of Orlando, Fla. as part number 1500115. The sensors 178, 180 and 182 are electrically connected to a pre-amplifier 184 which outputs the three analyzers analog sensor readings to a 32 bit microprocessor 188 for computation of gas concentrations as will be discussed in more detail hereafter.

When the first housing 68 and the second housing 154 are assembled, the unit 60 contains three optical paths which correspond to the three analyzers 62, 64 and 66. The first analyzer 62 contains the following optical path: the infrared source 126, the rotating cylinder 132, the sample cell 160, the filter 172 and the infrared sensor 178. The second analyzer 64 contains the following optical path: the infrared source 128, the rotating cylinder 132, the sample cell 162, the filter 174 and the infrared sensor 180. The third analyzer 66 contains the following optical path: the infrared source 124, the rotating cylinder 132, the sample cell 166, the filter 176 and the infrared sensor 182.

More specifically, the first analyzer 62 of the unit 60 is dedicated to the analysis of carbon dioxide (hereafter $CO_2$). Due to the wave fronts of the gases entering the unit 60, in this embodiment, it is desirable that the first analyzer 62 be dedicated to the analysis of $CO_2$. As discussed above with respect to the dimensions of the sample cell 18 of analyzer 10 of FIG. 1, the dimensions of the sample cell 160 of the first analyzer 62 are also are chosen so as to optimize both response time and sensitivity. A sample cell which is too long results in increased sensitivity however with decreased response time. A sample cell which is too short results in increased response time however with decreased sensitivity. The dimensions of the sample cell are thus chosen with proper consideration for response time and sensitivity and are selected between what would be the length that would provide either the best response time or the best sensitivity. The preferred dimensions of the sample cell 160 of the first analyzer 62 are as follows: 0.150"×0.225". $CO_2$ absorbs infrared energy in the range of between 4.2–4.36 microns. The filter 172 for the first analyzer 62 is chosen so as to include the absorption band of $CO_2$ as well as the two sidebands previously discussed and thus allows energy between 4.0 and 4.4 microns to pass through the filter 172 and be detected by the sensor 178.

The second analyzer 64 of the unit 60 shown in FIG. 2 is dedicated to the analysis of nitrous oxide (hereafter $N_2O$). The dimensions of the sample cell 162 are chosen on the same basis as the first analyzer 62 so as to optimize response time and sensitivity and preferably are as follows: 0.150"× 0.128". $N_2O$ absorbs infrared energy in the range of between 4.44–4.6 microns. The filter 174 for the second analyzer 64 is thus chosen to allow any energy between 4.4 and 4.8 microns to pass through the filter 174 and be detected by the sensor 180.

The third analyzer 66 of the unit 60 is substantially identical to the analyzer 10 of FIG. 1 in that it is dedicated to the analysis of the four anesthetic agents halothane, enflurane, isoflurane and sevoflurane. The dimensions of the sample cell 166 are identical to the dimensions of sample cell 18, and the chosen filter 176 is identical to the filter 24 earlier described.

As was the case with the analyzer 10 of FIG. 1, with the use of one filter, each analyzer 62, 64 and 66 of unit 60 employs one infrared source and one sample cell in one optical path so that there can be no difference in the sensor output for use as a reference of infrared source power output that with the sensor output for use as a gas absorption indicator. Thus, in order to determine changes in gas concentrations with one filter per analyzer, the rotating reference cells with known quantities of particular gases therein, are used for negative filtering the same way as the analyzer 10 of FIG. 1 uses negative filtering. The negative filtering reading when compared with the sensor reading without the negative filtering will give the total inband infrared energy after absorption which can then be expressed as a percentage of total inband power.

In the preferred embodiment, the three analyzers 62, 64 and 66 of the unit 60 shown in FIG. 2 share the rotating reference cells 143 in the cylinder 132 to minimize the size of unit 60. However, it should be noted that each analyzer 62, 64 and 66 could have its own set of reference cells. The cylinder 132 rotates within the recess 104 such that, at one time, only one reference cell 143 is aligned with any one of the optical paths of the three analyzers 62, 64 and 66. Therefore, the three analyzers 62, 64 and 66 function sequentially in that the optical path of the three analyzers 62, 64 and 66 is offset so that only one analyzer at a time has energy from its respective infrared source pass through a reference cell, sample cell filter then be detected by the infrared sensor of that analyzer.

The five reference cells 143 denoted herein as A, H, E, F and S contained in the rotating cylinder 132 contain known quantities of the gas(es) to be analyzed. For the gases set forth in the example, the reference cells A, H, E, F and S contain the following type and amount of gases at a pressure of 760 mm Hg:

| reference cell A = | 100.0% air | 760.0 mmHg |
|---|---|---|
| reference cell H = | 27.1% halothane | 205.9 mmHg |
| | 2.0% $N_2O$ | 15.2 mmHg |
| | 55.9% air | 424.9 mmHg |
| | 15.0% He | 114.0 mmHg |
| reference cell E = | 19.4% enflurane | 147.6 mmHg |
| | 2.0% $CO_2$ | 15.2 mmHg |
| | 2.0% $N_2O$ | 15.2 mmHg |
| | 61.6% air | 468.0 mmHg |
| | 15.0% He | 114.0 mmHg |
| reference cell F = | 26.1% isoflurane | 198.4 mmHg |
| | 2.0% $CO_2$ | 15.2 mmHg |
| | 56.9% air | 432.4 mmHg |
| | 15.0% He | 114.0 mmHg |
| reference cell S = | 17.4% sevoflurane | 132.2 mmHg |
| | 67.6% air | 513.8 mmHg |
| | 15.0% He | 114.0 mmHg |

Helium is included in reference cells H, E, F and S to determine leak rate. Helium does not effect the operation of the analyzer 10 for it does not absorb infrared energy.

The three analyzers 62, 64 and 66 are able to share a common set of reference cells A, H, E, F and S because the known quantity of $CO_2$ necessary for the operation of the first analyzer 62 can be in the same reference cell with the gases necessary for the operation of the second and third analyzers 64 and 66 and so forth because of the different frequencies of absorption of the gases to be analyzed of the three analyzers 62, 64 and 66.

One rotation of the cylinder 132 containing the five reference cells A, H, E, F and S results in five readings from the sensor 178 of the first analyzer 62, five readings from the sensor 180 of the second analyzer 64 and five readings from the sensor 182 of the third analyzer 66.

The operation of the three analyzers 62, 64 and 66 of the unit 60 and the method to analyze the gases are as follows. The operation of third analyzer 66 is the same as with FIG. 1 and will not be repeated here. Due to the similarity of the operation and method of the first and second analyzers 62 and 64 which analyze only one gas, only the operation of the first analyzer 62 will be detailed.

Per revolution of the cylinder 132 with the five reference cells A, H, E, F and S, the first analyzer 62 obtains five readings from the infrared sensor 178 as follows: $E_A$, $E_H$, $E_E$, $E_F$, $E_S$. The reading $E_A$ is the energy incident upon the sensor 178 when reference cell A is in the optical path of the first analyzer 62. With this reading, only the $CO_2$ present in the sample cell 160 is absorbing any energy from the infrared source 126. The readings $E_H$ and $E_S$ are not utilized because $CO_2$ was not present in reference cells H or S. $E_E$ and $E_F$ are the energies incident upon the sensor 178 when reference cells E and F respectively are in the optical path. In the preferred embodiment, equal amounts of $CO_2$ are present in reference cells E and F therefore the readings $E_E$ and $E_F$ should be the same thus creating a redundancy in analyzer 62. Redundant readings $E_E$ and $E_F$ will hereafter be preferred to as $E_{E/F}$. If these redundant readings do not agree, this is an indication that the analyzer 62 is malfunctioning.

It should be noted that it is only necessary to have a quantity of $CO_2$ in one of the reference cells. Further, if increased redundancy is desired, the same amount of $CO_2$ could be present in all four reference cells H, E, F and S.

Mathematically, the concentration of $CO_2$ in the sample cell 160 of the first analyzer 62 can be determined by the microprocessor 188 using the following equation:

$$\eta_{CO2} = \frac{1}{\alpha L_A} \ln \frac{\left(1 - \frac{E_{E/F}}{E_A}\right)\left(1 - \frac{\Delta V_a}{\Delta V_F}\right)}{\left(\frac{E_{E/F}}{E_A} - e^{-\alpha L_R \eta_R}\right)\left(\frac{\Delta V_a}{\Delta V_F}\right)}$$

where $n_{CO2}$=concentration of $CO_2$ in sample cell 160

$n_R$=concentration of $CO_2$ in reference cell E and F $\alpha$=absorption coefficient of $CO_2$ averaged over the absorption band $L_A$=length of sample cell 160

$L_R$=length of reference cell H, E, F or S $\Delta V_a$=frequency width of $CO_2$ absorption band $\Delta V_F$=frequency width of filter 172

$E_{E/F}$=energy incident upon the sensor 178 when reference cell E or F is in the optical path 190

$E_A$=energy incident upon the sensor 178 when reference cell A is in the optical path 190.

The equation is solved for the unknown $\eta_{CO2}$, the concentration of $CO_2$ in the sample cell 160 of the first analyzer 62.

Similarly, the concentration of $N_2O$ can be calculated using the five energy readings from the sensor 180 of the second analyzer 64 and the appropriate constants substituted in the above equation. The readings from sensor 180 can have the same redundancy as with the first analyzer 62 assuming the same quantity of $N_2O$ is present in various reference cells. In the preferred embodiment, equal amounts of $N_2O$ are present in reference cells H and E.

We claim:

1. A gas analyzer for analyzing a sample for a gas of interest, said analyzer comprising:

an infrared energy source;

a sensor for detecting infrared energy from said source, said infrared energy traveling between said source and said sensor defining an optical path;

a sample cell in said optical path comprising means for containing the sample to be analyzed;

at least two reference cells supported for selective positioning in said optical path, an infrared filter in said optical path, said filter being a wideband filter passing the absorption spectra of the gases of interest and additional spectra on each side of the absorption spectra of the gases of interest;

said sensor producing a signal representative of the energy remaining when each of said reference cells are alternately in said optical path;

means for determining the power output of the infrared energy source using the additional spectra passed by said filter; and a processor connected to said sensor whereby said processor receives said signals from said sensor and produces an output indicative of the concentration of the gas of interest in said sample cell.

2. A gas analyzer as set forth in claim 1 and further including a rotatable housing for supporting said reference cells so that said reference cells are selectively interposed in said optical path.

3. A gas analyzer as set forth in claim 2 and further including a motor connected to said housing for rotating said housing.

4. A method for analyzing a sample for multiple gases comprising the steps:
   (a) supplying a path of infrared energy produced by an infrared energy source;
   (b) interposing in said path a sample cell containing the sample to be analyzed;
   (c) interposing in said path one wideband and infrared filter that passes the absorption spectra of the multiple gases and additional sidebands;
   (d) detecting the infrared energy of said path after passage through said sample cell and said filter;
   (e) using said additional sidebands to determine the infrared energy source power output;
   (f) interposing in said path one of a plurality of reference cells, each reference cell containing a known quantity of a predetermined gas;
   (g) detecting the infrared energy of said path after passage through said sample cell, said reference cell and said filter;
   (h) producing a signal representative of said detected infrared energy of step (g); and
   (i) interposing the remainder of said plurality of reference cells one at a time in said path and repeating steps (g)-(h); and
   (j) processing said signals to determine whether and in what concentration the multiple gases are present in the sample.

5. A method for analyzing a sample for multiple gases as set forth in claim 4 in that the plurality of reference cells in step (f) equals one more than the number of multiple gases to be analyzed.

6. A method for analyzing a sample for multiple gases as set forth in claim 4 in that the sample cell of step (b) is downstream of the plurality of reference cells of step (f) in the path and the filter of step (c) is downstream of the sample cell of step (b) in the path.

7. A method for analyzing a gas mixture for gases of interest, said method comprising the steps:
   (a) producing a beam of infrared energy from an infrared energy source;
   (b) positioning in said beam a sample cell containing the gas mixture;
   (c) positioning in said beam an infrared filter that passes a greater bandwidth of energy than the absorption spectra of the gases of interest;
   (d) detecting the remaining infrared energy after said beam passes through said sample cell and said filter;
   (e) determining the infrared energy source power output based upon the detected energy in step (d);
   (f) positioning one of a plurality of reference cells in said beam, each of said reference cells filled with a known quantity of a predetermined gas;
   (g) detecting the remaining infrared energy after said beam has passed through said sample cell, said reference cell and said filter;
   (h) generating a signal representative of the detected remaining energy of step (g);
   (i) positioning the others of said plurality of reference cells one at a time in said path and repeating steps (g)-(h); and
   (j) determining the presence and concentration of the gases of interest using negative filtering with the signals generated in step (h) and with the infrared energy source power output from step (e).

8. A method for analyzing a gas mixture for gases of interest as set forth in claim 7 wherein said plurality of reference cells is one more than the number of multiple gases to be analyzed.

9. A method for analyzing a gas mixture for a gas of interest, said method comprising the steps:
   (a) producing a beam of infrared energy from an infrared energy source;
   (b) positioning in said beam a sample cell containing the gas mixture;
   (c) positioning in said beam an infrared filter that passes the absorption spectra of the gas of interest and that additionally passes two sidebands of energy;
   (d) using said sidebands to determine the infrared energy source power output;
   (e) alternately positioning each of a plurality of reference cells in said beam, each of said plurality of reference cells containing a known quantity of a predetermined gas;
   (f) detecting the level of the infrared energy of said beam after it passes through said sample cell, said filter and alternately each of said reference cells; and
   (g) processing said detected levels from step (f) and said infrared energy source power output to determine the presence and concentration of the gas of interest.

* * * * *